United States Patent [19]

Baker

[11] Patent Number: 4,670,250

[45] Date of Patent: Jun. 2, 1987

[54] DURABLE CONTROLLED RELEASE MICROCAPSULES

[75] Inventor: Richard W. Baker, Menlo Park, Calif.

[73] Assignee: Bend Research, Inc., Bend, Oreg.

[21] Appl. No.: 544,251

[22] Filed: Oct. 21, 1983

[51] Int. Cl.⁴ .......................... A61K 9/30; A61K 9/50
[52] U.S. Cl. ......................................... 424/419; 427/3; 424/19; 424/20; 424/33; 514/963; 71/DIG. 1; 523/122; 523/102; 264/4.3; 261/24
[58] Field of Search ............................. 424/31, 32, 33; 514/963

[56] References Cited

U.S. PATENT DOCUMENTS

| | | | |
|---|---|---|---|
| 3,660,304 | 5/1972 | Matsukawa et al. | 252/316 |
| 3,691,090 | 9/1972 | Kitajima et al. | 424/32 |
| 3,859,228 | 1/1975 | Morishita et al. | 424/33 |
| 3,891,570 | 6/1975 | Fukushima et al. | 424/33 |
| 3,943,063 | 3/1976 | Morishita et al. | 424/33 |
| 3,960,757 | 6/1976 | Morishita et al. | 424/32 |
| 4,089,800 | 5/1978 | Temple | 424/33 |
| 4,172,119 | 10/1979 | Kuchner et al. | 424/32 |
| 4,217,241 | 8/1980 | Okada et al. | 424/33 |
| 4,389,330 | 6/1983 | Tice et al. | 424/33 |
| 4,568,559 | 2/1986 | Nuwayser et al. | 424/31 |

OTHER PUBLICATIONS

The Merch Index, 9th Edition, pp. 435.
CA 97:140223c Efficacy of Microencapsulated Diazinon against German Cockroach Blaltella Germanica, 1982.

Primary Examiner—Ronald W. Griffin
Attorney, Agent, or Firm—Chernoff, Vilhauer, McClung & Stenzel

[57] ABSTRACT

Impact-resistant microcapsules for the sustained and controlled release of biologically active ingredients through a surrounding permeable polymeric wall are disclosed wherein the ratio by weight of active ingredient to polymer is from about 4:1 to about 1:4, the polymeric walls having high tensile yield and tensile impact strengths and low nitrogen permeabilities.

12 Claims, 4 Drawing Figures

RELEASE OF DISPARLURE FROM POLYSULFONE MICROCAPSULES, 25°C.
INITIAL LOADING: 42 mg/100mg.

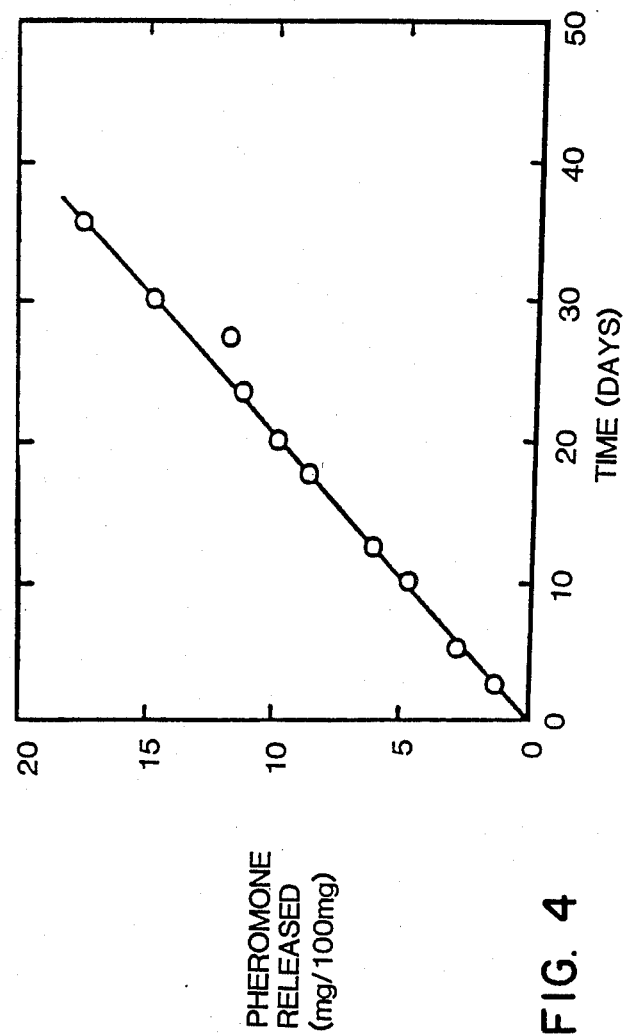

DURABLE CONTROLLED RELEASE MICROCAPSULES

BACKGROUND OF THE INVENTION

Microencapsulation of various core materials in polymers by nonreactive processes such as solvent evaporation and phase separation is known. See, for example, U.S. Pat. Nos. 3,657,144 to Yoshida, 3,732,172 to Herbig et al., 3,523,906 to Vrancken et al., 3,960,757 to Morishita, et al., and 3,660,304 to Matsukawa. The Yoshida '144 patent discloses a process for encapsulating discrete solid particles or droplets of aqueous liquids and the Herbig et al. '172 patent also discloses encapsulation of solid particles. The Vrancken et al. '906 patent discloses encapsulation of water droplets or compounds dissolved or dispersed in water, while the Morishita, et al. '757 patent discloses bioerodible or sustained release microcapsules of medicaments. The Matsukawa '304 patent discloses encapsulation of oily liquids in thermosetting resin-type polymers, designed for the release of dyes upon fracturing of the polymer shell, the encapsulation being accomplished by mixing a solution of a low boiling point solvent and a hydrophobic polymer with a high boiling point solvent, emulsifying and evaporating the low boiling point solvent. These processes are primarily physical and do not involve chemical reactions, thus allowing the use of more varied polymeric materials for the microcapsule walls, avoiding the necessity of a separate crosslinking or strengthening step, and enabling the encapsulation of labile or reactive ingredients that cannot be encapsulated via processes such as interfacial polymerization.

Controlled release of biologically active microencapsulated ingredients is also known. See, for example, U.S. Pat. Nos. 4,316,884, 4,172,119, 4,056,610 and 3,977,922, as well as J. Chem. Ecol. 7 (1981) 867, and Scher, "*Controlled Release Pesticides,*" 53 ACS Symposium Series, Chapter 12 (1977). However, the duration of biological activity disclosed is generally limited to a period of from a few days to a month.

There is, therefore, a need for a controlled release microcapsule capable of providing sustained release of biologically active core ingredients at a substantially constant rate over an extended period of time through a strong, impact-resistant, yet permeable polymeric shell. Such strong, impact-resistant, and permeable microcapsules would be extremely useful for agricultural applications where the microcapsules must be applied by spraying with pumps and nozzles, which subjects the microcapsules to high shear forces, and where long-term delivery, i.e., up to six months and more, of the biologically active ingredient is desirable. Such microcapsules would also be useful for delivery of pharmaceuticals, flavors, sweeteners, and the like in chewable formulations where again the microcapsules are subjected to high forces and fracture is to be avoided.

It is therefore a principal object of this invention to provide novel microcapsules for the sustained and controlled release of biologically active core ingredients through a durable, impact-resistant, permeable polymeric shell.

SUMMARY OF THE INVENTION

According to the present invention, highly durable controlled-release microcapsules are provided which are capable of releasing biologically active core ingredients over an extended period of time at a relatively constant rate by using certain thermoplastic nonporous polymers with biologically active core ingredients (hereafter referred to as "active ingredients") in a ratio of from about 1:4 to about 4:1 by weight. The thermoplastic polymers are essentially nonporous, have a tensile yield strength of more than 9,000 lb/in$^2$ (ASTM test D638), a tensile impact strength of more than 70 ft-lb/in$^2$ (ASTM test D1822), a permeability to nitrogen, or nitrogen permeability, of less than $10^{-10}$ cm$^3$-cm/cm$^2$-sec-cmHg and are soluble in organic solvents useful in simple unreactive microencapsulation processes such as solvent evaporation or phase separation.

BRIEF DESCRIPTION OF THE DRAWINGS

FIGS. 1-4 are graphs showing biological activity or rates of release over time of various active ingredients by the microcapsules of the present invention.

DETAILED DESCRIPTION OF THE INVENTION

Figure 1:
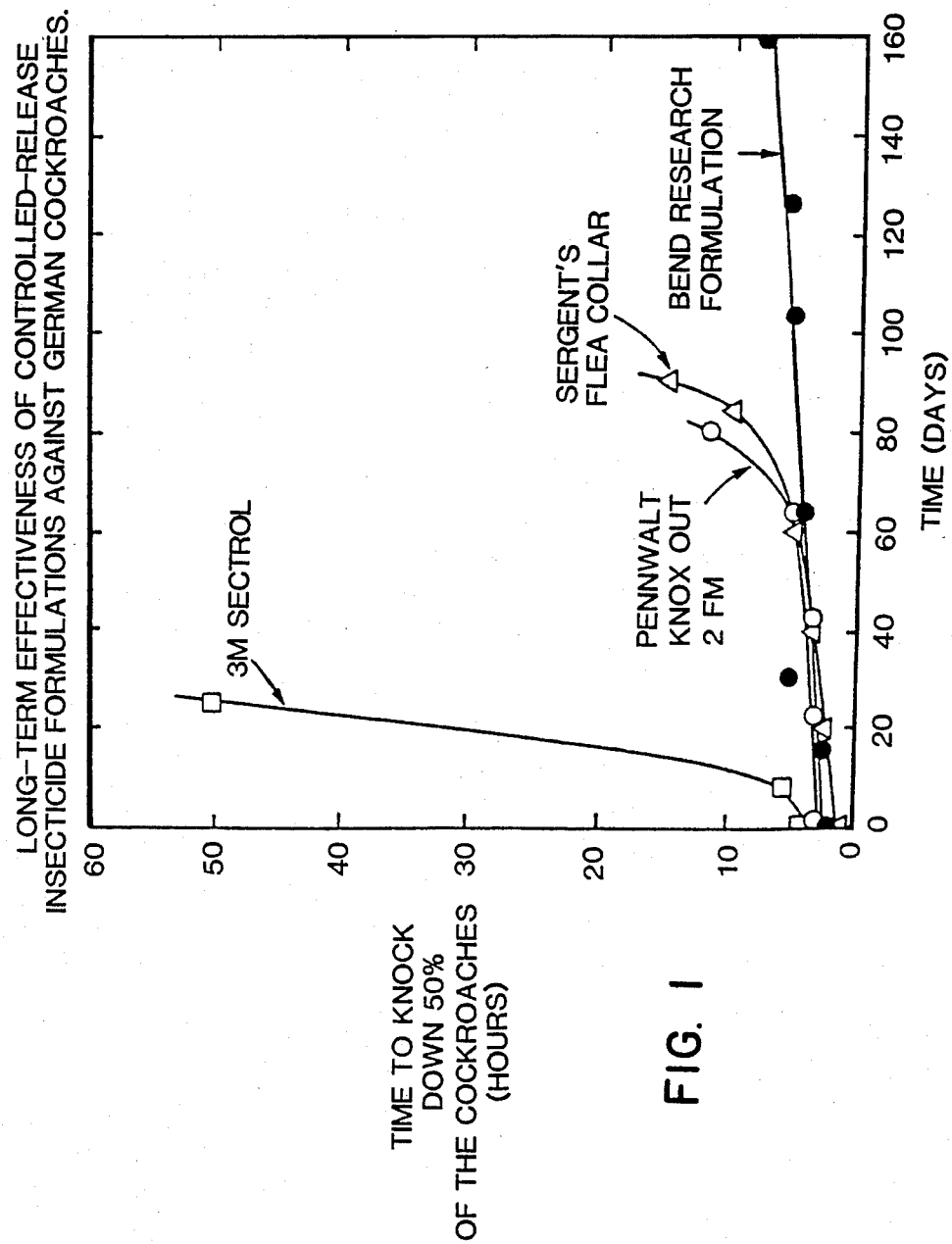

The controlled-release microcapsules of the present invention comprise a core of active ingredient and a durable, impact-resistant, low-permeability thermoplastic polymer surrounding the core in a generally spherical shape and in dimensions on the order of 5-500 microns in diameter. The active ingredient is released at a slow and relatively constant rate over an extended period of time, the rate being determined by the permeability of the polymeric shell to the active ingredient, and by the thickness of the polymeric shell, which in turn is determined by the ratio of core or active ingredient to polymer. The range of ratios of core to polymer discovered to yield the controlled-release microcapsules of the present invention is from about 4:1 to about 1:4 by weight, this range resulting in both sufficiently high loading and sufficiently sustained release of the active ingredient.

The active ingredients of the controlled-release microcapsules of the present invention are, generally speaking, biologically active, or capable of effecting changes on life forms, be they plant, animal or microscopic life. For this reason, in most cases, it is quite important to deliver sufficient quantities of active ingredients over a sufficiently prolonged period of time to achieve the proper effect of the active ingredients. Active ingredients suitable for release by the microcapsules of the present invention include, without limitation, pheromones, insecticides, herbicides, fertilizers, pharmaceuticals, deodorants, fragrances, and flavors. They are generally nonaqueous, hydrophobic and organic and include liquids and solids that are soluble in the organic solvent used in the preferred methods of preparing the microcapsules of the invention. The active ingredient may be an aqueous hydrophilic or inorganic substance so long as it is emulsified or dispersed, but not dissolved, in a nonaqueous, hydrophobic, organic liquid that is encapsulated. Suitable pheromones include disparlure, gossyplure, virelure, muscalure, grandlure, japonilure, trimedlure, codlure and periplanone B. Suitable insecticides include naled, dimpylate, propoxur chlorpyrifos, malathion, methyl parathion, carbaryl, methomyl, permethrin, fenvalerate and dichlorvos.

In preparing the controlled release microcapsules of the present invention, it is essential that the activity of the active ingredient remain substantially constant, or as nearly at unity as possible. Since the principal driving force for the release of the active ingredient is the relative concentration or activity of the active ingredient in the core of the microcapsule, the active ingredient may not be in solution in the completed microcapsule since that would substantially reduce its relative concentration or activity, and so render the microcapsules substantially less effective for controlled release applications.

The encapsulating permeable polymer of the present invention should be essentially nonporous, strong, impact-resistant, have a low permeability to the active ingredient and be soluble in organic solvents used in the preferred methods of manufacture. The tensile yield strength should preferably be higher than about 9,000 lb/in$^2$, and the tensile impact strength should preferably be higher than 70 ft-lb/in$^2$. The permeability to the active ingredient depends on the preferred duration of release. As a general measure of permeability, polymers with a nitrogen permeability of less than $10^{-10}$ cm$^3$-cm/cm$^2$-sec-cmHg would be suitable for longlasting release of most active ingredients, although in some cases higher permeabilities may be preferred.

Examples of preferred organic solvents in at least one of which the polymer should be soluble include methylene chloride, chloroform, carbon tetrachloride, tetrahydrofuran, methyl ethyl ketone, acetone, methanol, ethanol, acetonitrile, acrylonitrile, furan, butyraldehyde, diethylamine, carbon disulfide, hexane, cyclohexane, benzene, ethyl acetate, butyl acetate, dichloroethane, trichloroethane, dimethyl formamide, dimethyl acetamide, and mixtures thereof.

Listed in the Table are examples of useful polymers together with their key properties. They include appropriate grades of the following classes of nonporous polymers: polysulfones, including polyether sulfones and polyaryl sulfones, polycarbonates, polymethylmethacrylates, poly(styrene-acrylonitriles), polystyrenes, acrylonitrile-butadiene-styrene polymers, polyacrylonitriles, polyvinyl fluorides, polyvinylidene fluorides, polyvinyl chlorides, polyvinylidene chlorides, polyethyleneterephthalates, polybutyleneterephthalates, polyamides, polyamide-imides, polyimides, polyacetals, cellulose esters, polyurethanes, polyarylates, polyaryl ethers, and derivatives or copolymers of the above.

organic solvents and therefore cannot be used in simple, unreactive microencapsulation processes. Only those grades of these polymers that satisfy the above-mentioned requirements are satisfactory for use in the preparation of the controlledrelease microcapsules of the present invention.

Although the solvent evaporation process described below is the preferred method of preparing the controlled-release microcapsules of the present invention, they may also be prepared by other known solvent evaporation or phase separation methods. In the preferred method, the active ingredient and polymer are both dissolved in the weight ratio of from about 4:1 to about 1:4 in a generally low boiling point organic solvent of the type described above. The solvent should be capable of dissolving both the active ingredient and the polymer during the course of preparation of the microcapsules, and should be immiscible with the emulsification liquid.

The solution of active ingredient and polymer in the organic solvent is then emulsified in a relatively high boiling point liquid, generally having a boiling point at least about 20° C. higher than that of the organic solvent. In addition, the emulsification liquid may contain a surfactant to aid in emulsification. Water is the preferred liquid, although others such as silicone oils, perfluorinated hydrocarbons, ethylene glycol, and formamide may also be used. The surfactant may be gelatin, polyoxyethylene derivatives, or any of a number of commercially available products.

The preferred concentration of polymer in the solvent is between about 5% and about 20% by weight, although other concentrations may be used. The preferred combined concentration of the active ingredient, polymer and organic solvent in the immiscible liquid should be less than about 20% by weight. Emulsification is preferably performed at a temperature of between about 0° C. and 40° C. Solvent evaporation is then effected by raising the temperature of the liquid vehicle to a temperature preferably ranging from about 20° C. lower than the solvent boiling point to about 10° C. above the solvent boiling point. Stirring is continued until substantially all of the solvent has evaporated. The completely formed microcapsules are then collected by

TABLE

| Polymer | Tensile Yield Strength* (lb/in$^2$) | Tensile Impact Strength** (ft-lb/in$^2$) | Permeability to N$_2$ $10^{-10}\left(\dfrac{\text{cm}^3\text{-cm}}{\text{cm}^2\text{-sec-cmHg}}\right)$ |
|---|---|---|---|
| Polysulfone | 10,200–14,000 | 200–250 | 0.2 |
| Polycarbonate | 7,500–11,200 | 150–350 | 0.3 |
| Nylon | 3,000–14,000 | 40–400 | 0.01 |
| Polymethylmethacrylate | 4,000–17,000 | 20–90 | ~0.5 |
| Poly(styreneacrylonitrile) | 9,000–12,000 | 20–100 | 0.05 |

*ASTM test D638
**ASTM test D1822

It should be noted that of the above-mentioned classes of polymers found to be useful in the invention, only certain grades of these polymers simultaneously satisfy the requirements of high tensile yield strength, high tensile impact strength, low permeability, and solubility in a common organic solvent. For example, most polystyrenes have high tensile yield strength but low tensile impact strength; many polymethylmethacrylates, altough soluble in common organic solvents, have neither sufficiently high tensile yield strength nor sufficiently high tensile impact strength; many polyamides, including most nylons, are not soluble in common filtration, centrifugation, settling, or other conventional method, and can be stored either wet or dry.

EXAMPLES

Example 1

2 g of polycarbonate having a tensile yield strength of 10,200 lb/in$^2$ (ASTM test D638), a tensile impact strength of 350 ft-lb/in$^2$ (ASTM test D1822) and a nitrogen permeability of $0.3 \times 10^{-10}$ cm$^3$-cm/cm$^2$-sec-cmHg (Merlon ®M-39 manufactured by Mobay Corp. of Pittsburgh, Pennsylvania) and 2 g of the insecticide naled were dissolved in 20 ml of methylene chloride at room temperature. This solution was then emulsified in 500 ml of water containing 1% by weight gelatin and was stirred continuously for two hours at 45° C. until all of the methylene chloride had evaporated. The microcapsules were then collected by filtration and dried at room temperature. The naled loading of the microcapsules was determined to be 48% by weight. FIG. 1 shows that the long-term effectiveness against German cockroaches of naled from these microcapsules was up to six months. For purposes of comparison, the same amounts of the commercially available microencapsulated insecticides Knox-Out®2FM from Pennwalt Corporation, Sectrol® from 3M Corporation and non-microencapsulated but controlled-release naled from Sargeant's® Flea Collar, under the same conditions, effectively released insecticide for periods of, respectively, only three months, one month and three months, as shown in FIG. 1.

Example 2

Figure 2:
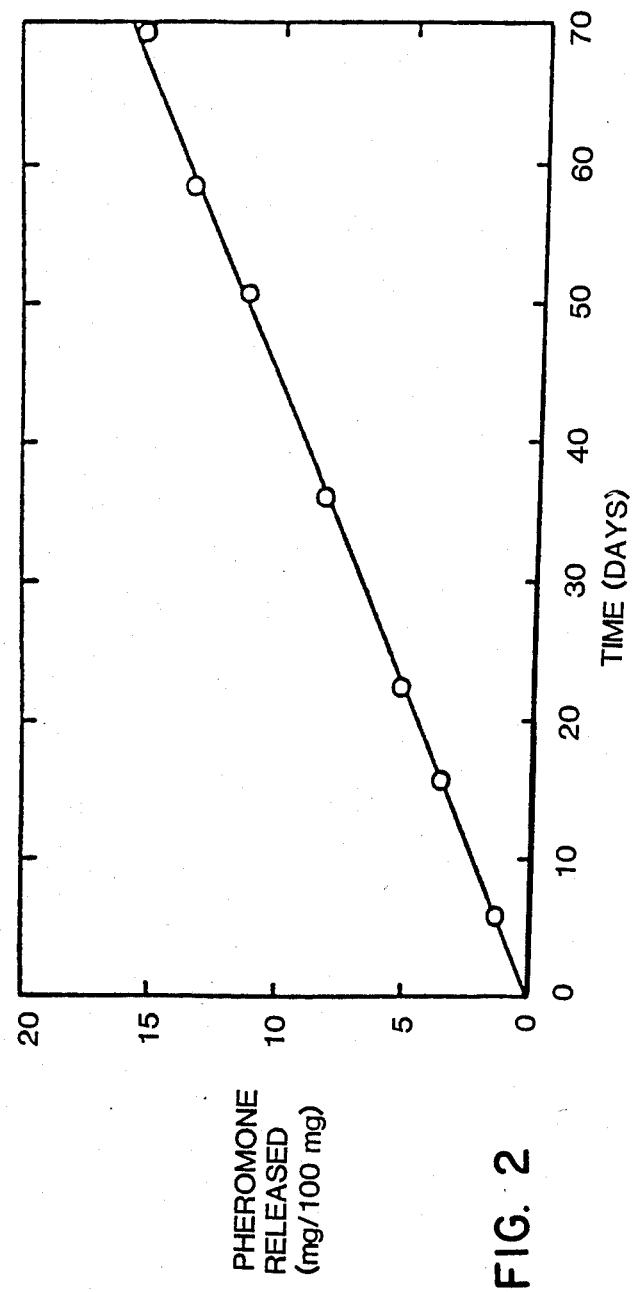

2.5 g of polysulfone having a tensile yield strength of 10,200 lb/in$^2$ (ASTM test D638), a tensile impact strength of 200 ft-lb/in$^2$ (ASTM test D1822), and a nitrogen permeability of $0.2 \times 10^{-10}$ cm$^3$-cm/cm$^2$-sec-cmHg (Udel®P-3500 manufactured by Union Carbide of New York, New York) and 2.5 g of disparlure (the gypsy moth pheromone) were dissolved in 25 ml of methylene chloride at room temperature. This solution was then emulsified in 500 ml of water containing 1% by weight gelatin and was stirred continuously for two hours at 45° C. until all of the methylene chloride had evaporated. The microcapsules were collected by filtration and dried at room temperature. The disparlure loading was determined to be 42% by weight. FIG. 2 shows the release of disparlure from these microcapsules plotted against time. Based on the initial loading, the microcapsules exhibited an effective duration of greater than 150 days. In contrast, prior art microcapsules have been shown to release disparlure for only about 30 days, J. Chem. Ecol. 7 (1981) 867.

Example 3

Figure 3:
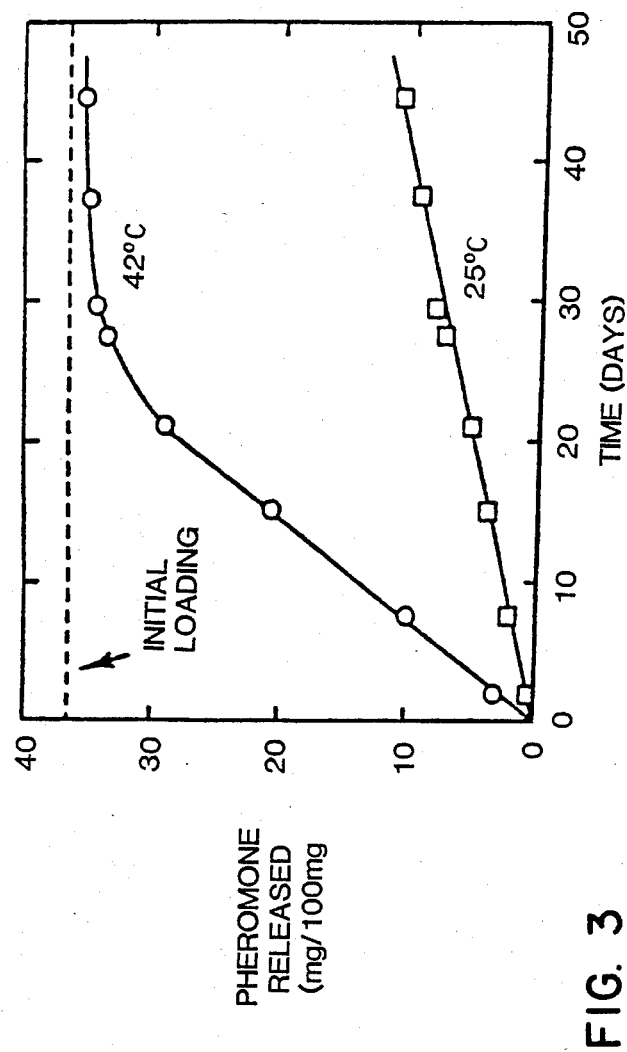

10 g of the same type of polysulfone as used in Example 2 and 8.6 g of gossyplure (the pink bollworm pheromone) were dissolved in 100 ml of methylene chloride at room temperature. This solution was then emulsified in 150 ml water and was then added to 5.1 liters of water containing 0.5% by weight gelatin and 0.005% by weight polyoxyethylene (Pluronic®31R2—surfactant manufactured by BASF Wyandotte), and was stirred at room temperature. Five additional polysulfone/gossyplure/methylene chloride solutions were similarly prepared, emulsified as above, and added to the same 5.1 liters of water. This solution was then stirred for two hours at 45° C. until all of the solvent had evaporated. The microcapsules were collected by filtration and dried at room temperature. The gossyplure loading in the microcapsules was determined to be 36% by weight, and the total yield was 90 g of microcapsules. FIG. 3 shows the release of gossyplure from the microcapsules plotted against time.

These same microcapsules were suspended in water and sprayed onto cotton fields from a Grumman Ag-Cat airplane conventionally equipped with a wind driven pump and 58 standard nozzles with size 6 orifices. The pressure was maintained at 30 psi to yield an application volume rate of three gallons per acre and a 48 foot swath width. The microcapsules successfully prevented 94-97% of the mating of pink bollworm moths for the entire duration of the 15 day test, indicating no damage whatsoever to the microcapsules by the pumping and spraying apparatus. In contrast, prior art microcapsules require a separate plastic coating to improve durability sufficiently for spraying. See, for example, J. R. Plimmer et al., *Proceedings* 1976 International Controlled Release Pesticide Symposium, Akron, Ohio, Sept. 13, 1976, Pages 3.29-3.39.

Example 4

2 g of poly(styrene-acrylonitrile) (30% acrylonitrile) having a tensile yield strength of greater than 10,000 lb/in$^2$ (ASTM test D638), a tensile impact strength of greater than 70 ft-lb/in$^2$ (ASTM test D1822), and a nitrogen permeability of $0.05 \times 10^{-10}$ cm$^3$-cm/cm$^2$-sec-cmHg and 1.7 g of gossyplure were dissolved in 20 ml of methylene chloride. The microcapsules were prepared as in Example 2. The gossyplure loading was determined to be 33% by weight. FIG. 4 shows the release of gossyplure from the microcapsules plotted against time.

The terms and expressions which have been employed in the foregoing specifications are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A controlled release microcapsule comprising a core of active ingredient and a permeable polymer surrounding said core,
   (a) the active ingredient being biologically active,
   (b) the permeable polymer being thermoplastic and soluble in a common organic solvent, having a tensile yield strength of more than 9,000 lb/in$^2$, a tensile impact strength of more than 70 ft-lb/in$^2$, and a nitrogen permeability of less than $10 \times 10^{10}$ cm$^3$-cm/cm$^2$-sec-cmHg, and
   (c) having a core-to-polymer ratio from about 4:1 to about 1:4 by weight.

2. The microcapsule of claim 1 wherein the polymer is selected from polysulfones, polyether sulfones, polyaryl sulfones, polycarbonates, polymethylmethacrylates, poly(styrene-acrylonitriles), polystyrenes, acrylonitrilebutadiene-styrene polymers, polyacrylonitriles, polyvinyl fluorides, polyvinylidene fluorides, polyvinyl chlorides, polyvinylidene chlorides, polyethyleneterephthalates, polybutyleneterephthalates, polyamides, polyamideimides, polyimides, polyacetals, cellulose esters, polyurethanes, polyarylates, polyaryl ethers, and derivatives or copolymers thereof.

3. The microcapsule of claim 1 wherein the polymer is selected from polysulfones, polyether sulfones and polyaryl sulfones.

4. The microcapsule of claim 1 wherein the polymer is a polycarbonate.

5. The microcapsule of claim 1 wherein the polymer is a polymethylmethacrylate.

6. The microcapsule of claim 1 wherein the polymer is a poly(styrene-acrylonitrile).

7. The microcapsule of claim 1 wherein the polymer is selected from polyamides and polyamide-imides.

8. The microcapsule of claim 1 wherein the active ingredient is selected from pheromones, insecticides, herbicides, fertilizers, pharmaceuticals, deodorants, fragrances, and flavors.

9. The microcapsule of claim 1 wherein the active ingredient is a pheromone.

10. The microcapsule of claim 9 wherein the pheromone is selected from disparlure, gossyplure, virelure, muscalure, grandlure, japonilure, trimedlure, codlure and periplanone B.

11. The microcapsule of claim 1 wherein the active ingredient is an insecticide.

12. The microcapsule of claim 11 wherein the insecticide is selected from naled, dimpylate, propoxur, chlorpyrifos, malathion, methyl parathion, carbaryl, methomyl, permethrin, fenvalerate and dichlorvos.

* * * * *

UNITED STATES PATENT AND TRADEMARK OFFICE
CERTIFICATE OF CORRECTION

PATENT NO. : 4,670,250

DATED : June 2, 1987

INVENTOR(S) : Richard W. Baker

It is certified that error appears in the above-identified patent and that said Letters Patent is hereby corrected as shown below:

Col. 4, line 5    Change "controlledrelease" to --controlled release--

Col. 6, line 41   Change "10x10cm$^3$" to --$10^{-10}$cm$^3$--

Signed and Sealed this

Twenty-second Day of March, 1988

Attest:

DONALD J. QUIGG

Attesting Officer        Commissioner of Patents and Trademarks